United States Patent
Goldsmith et al.

(10) Patent No.: US 9,678,276 B1
(45) Date of Patent: Jun. 13, 2017

(54) ALL-GLASS ON-CHIP HIGH QUALITY-FACTOR OPTICAL MICRORESONATOR

(71) Applicant: Wisconsin Alumni Research Foundation, Madison, WI (US)

(72) Inventors: Randall Howard Goldsmith, Madison, WI (US); Kassandra Ann Knapper, Madison, WI (US); Kevin Daniel Heylman, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 14/990,296

(22) Filed: Jan. 7, 2016

(51) Int. Cl.
| G02B 6/10 | (2006.01) |
| G02B 6/293 | (2006.01) |
| G01N 21/77 | (2006.01) |
| G02B 6/12 | (2006.01) |
| G02B 6/13 | (2006.01) |

(52) U.S. Cl.
CPC ..... G02B 6/29341 (2013.01); G01N 21/7746 (2013.01); G02B 6/12004 (2013.01); G02B 6/13 (2013.01); G01N 2201/08 (2013.01); G02B 2006/12038 (2013.01); G02B 2006/12169 (2013.01)

(58) Field of Classification Search
USPC .................................................. 385/14, 131
See application file for complete search history.

(56) References Cited

U.S. PATENT DOCUMENTS

| 5,825,799 A * | 10/1998 | Ho ........................ B82Y 20/00 372/108 |
| 7,781,217 B2 | 8/2010 | Armani | |
| 8,818,146 B2 * | 8/2014 | Vahala .................. G02B 6/136 385/129 |
| 2005/0111776 A1 * | 5/2005 | Martin ............... G02B 6/12007 385/14 |
| 2005/0163185 A1 * | 7/2005 | Vahala ............... G02B 6/29341 372/67 |

(Continued)

OTHER PUBLICATIONS

D. K. Armani et al., Ultra-high-Q toroid microcavity on a chip, Nature, vol. 421, Feb. 27, 2003, pp. 925-928.

(Continued)

*Primary Examiner* — Eric Wong
(74) *Attorney, Agent, or Firm* — Bell & Manning, LLC (57) ABSTRACT

Optical microresonator platforms are provided comprising a substrate having a surface, a plurality of $SiO_2$ pillars, and a plurality of $SiO_2$ whispering gallery mode (WGM) optical microresonators, each $SiO_2$ pillar extending from the surface of the substrate and terminating in a corresponding $SiO_2$ WGM optical microresonator of the plurality of $SiO_2$ WGM optical microresonators, wherein the substrate, the plurality of $SiO_2$ pillars and the plurality of $SiO_2$ WGM optical microresonators form a monolithic structure, and further wherein the substrate is substantially transparent to visible light. The substrate may be a $SiO_2$ substrate and the $SiO_2$ WGM optical microresonator may be a $SiO_2$ optical microtoroid.

20 Claims, 10 Drawing Sheets

(56) References Cited

U.S. PATENT DOCUMENTS

2012/0281957 A1* 11/2012 Chamanzar ............ B82Y 20/00
                                                                                                                    385/131
2015/0234211 A1     8/2015 Goldsmith
2015/0362425 A1    12/2015 Goldsmith

OTHER PUBLICATIONS

Matthew Borselli et al., Rayleigh scattering, mode coupling, and optical loss in silicon microdisks, Applied Physics Letters, vol. 85, No. 17, Oct. 25, 2004, pp. 3693-3695.
V.B. Braginsky et al., Quality-Factor and Nonlinear Properties of Optical Whispering-Gallery Modes, Physics Letters A, vol. 137, No. 7, 8, May 29, 1989, pp. 393-397.
Kevin D. Heylman et al., Photothermal Microscopy of Nonluminescent Single Particles Enabled by Optical Microresonators, J. Phys. Chem. Lett., 5, May 16, 2014, pp. 1917-1923.
Mani Hossein-Zadeh et al., Free ultra-high-Q microtoroid: a tool for designing photonic devices, Optics Express vol. 15, No. 1, Jan. 8, 2007, pp. 166-175.
J.-B. Jager et al., High-Q silica microcavities on a chip: From microtoroid to microsphere, Applied Physics Letters 99, 181123, Nov. 4, 2011, pp. 1-4.
Bo Peng et al., Photonic molecules formed by coupled hybrid resonators, Opt. Lett. 37, May 2, 2013, pp. 3435-3437.
Kassandra Ann Knapper, Designing and Fabricating All-Glass Toroidal Microresonators for Single-Molecule Photothermal Spectroscopy, Presentation given at the University of Wisconsin-Madison, Mar. 11, 2015, pp. 1-47.
A. Serpenguzel et al., Excitation of resonances of microspheres on an optical fiber, Optics Letters, vol. 20, No. 7 , Apr. 1, 1995, pp. 654-656.
F. Vollmer et al., Protein detection by optical shift of a resonant microcavity, Applied Physics Letters, vol. 80, No. 21, May 27, 2002, pp. 4057-4059.
Xiaomin Zhang et al., Silica microtoroid resonator sensor with monolithically integrated waveguides, Optics Express, vol. 21, No. 20, Oct. 7, 2013, pp. 23592-23603.

\* cited by examiner

ALL-GLASS ON-CHIP HIGH QUALITY-FACTOR OPTICAL MICRORESONATOR

REFERENCE TO GOVERNMENT RIGHTS

This invention was made with government support under N66001-12-1-4215 awarded by the DOD/DARPA and DMR1121288 awarded by the National Science Foundation. The government has certain rights in the invention.

BACKGROUND

Label-free sensing methods have the potential to enable detection and characterization of chemical species at the single-molecule level without the aid of probes or modifications to the target of interest. Such a capability would have broad applicability to medical diagnostics, toxicology, and chemical quantification. Label-free imaging strategies offer additional possibilities in the context of revealing organization of biological and materials systems over a range of length scales. Whispering gallery mode (WGM) optical microresonators have been shown to be a highly effective platform for label-free sensing, reaching the single protein and single nucleotide level, and enabling label-free imaging of non-emissive particles. Light is evanescently coupled into WGM resonators at specific resonant wavelengths and will circulate many times, allowing the mode to repeatedly sample the surface of the resonator, making these devices highly sensitive to changes in microenvironment. Additionally, the surface can be functionalized with receptors, antibodies, DNA complements, etc, to enable chemical selectivity.

While a variety of microresonators—including microspheres, microrings, nanofibers, photonic crystal cavities and Fabry-Perot resonators—have been used for sensing applications, microtoroid and microsphere resonators have shown the highest levels of sensitivity, including reaching the single molecule limit. This success derives from two superior properties: their high quality (Q) factor and low mode volume (V), with the ratio Q/V ratio dictating the sensitivity. Microtoroid resonators possess the additional advantages of on-chip fabrication, a critical requirement for large-scale fabrication, and a mode spectrum of substantially reduced complexity. The lithographic fabrication of $SiO_2$-on-Si microtoroids takes advantage of material contrast to execute the fabrication: a silica resonator atop a silicon pillar and substrate. However, fabrication of an oxide microresonator on a silicon pillar uses a highly stochastic laser-induced reflow step for smoothing the rim and limiting scattering losses. The laser reflow process must be conducted on each individual microtoroid, introducing complexity and heterogeneity into the process and ultimately preventing wafer-scale fabrication.

It has been shown that the sensitivity of microtoroid resonators to their microenvironment can be exploited to enable a platform for label-free single-particle microscopy. Small changes to the refractive index at the surface of the microresonator result in a shift of the resonant frequency. Because changes in the refractive index are proportional to the local temperature, the resonance shift can be used as an indicator of local temperature change at a point on the surface of the resonator. Microresonators are thus extraordinarily sensitive thermometers, including quantification of the thermal energy dissipated from a relaxing molecule after optical excitation. Microtoroids are a highly suitable platform for conducting these measurements because the Q/V ratio minimizes the volume that needs to be heated, as well as provides the ultra-narrow linewidth required to distinguish minute resonance shifts.

SUMMARY

Provided herein are optical microresonator platforms and methods for fabricating the platforms.

In one aspect, an optical microresonator platform is provided comprising a substrate having a surface, a plurality of $SiO_2$ pillars, and a plurality of $SiO_2$ whispering gallery mode (WGM) optical microresonators, each $SiO_2$ pillar extending from the surface of the substrate and terminating in a corresponding $SiO_2$ WGM optical microresonator of the plurality of $SiO_2$ WGM optical microresonators, wherein the substrate, the plurality of $SiO_2$ pillars and the plurality of $SiO_2$ WGM optical microresonators form a monolithic structure, and further wherein the substrate is substantially transparent to visible light.

In another aspect, an optical microresonator platform is provided comprising a substrate having a surface, a $SiO_2$ pillar extending from the surface of the substrate and terminating in a $SiO_2$ optical microtoroid, wherein the substrate, the $SiO_2$ pillar and the $SiO_2$ optical microtoroid form a monolithic structure, and further wherein the substrate is substantially transparent to visible light.

In another aspect, a method of fabricating an optical microresonator platform is provided, the method comprising: patterning a layer of silicon which has been formed on a surface of a $SiO_2$ substrate to form a plurality of silicon islands on the surface of the $SiO_2$ substrate; removing a portion of the $SiO_2$ substrate under each silicon island of the plurality of silicon islands to form a plurality of $SiO_2$ pillars, each $SiO_2$ pillar supporting a corresponding silicon island of the plurality of silicon islands; and thermally oxidizing each silicon island of the plurality of silicon islands to convert the silicon of the silicon island to $SiO_2$ to form a plurality of $SiO_2$ WGM optical microresonators. The method provides the optical microresonator platform comprising the $SiO_2$ substrate having the surface, the plurality of $SiO_2$ pillars, and the plurality of $SiO_2$ WGM optical microresonators, each $SiO_2$ pillar extending from the surface of the $SiO_2$ substrate and terminating in a corresponding $SiO_2$ WGM optical microresonator of the plurality of $SiO_2$ WGM optical microresonators, wherein the $SiO_2$ substrate, the plurality of $SiO_2$ pillars and the plurality of $SiO_2$ WGM optical microresonators form a monolithic structure.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIGS. 2A-2B show SEM images of all-glass toroids.

FIGS. 9A-9C show a photothermal mapping experiment of gold nanorods (40 nm×80 nm) adsorbed to the surface of an all-glass toroid according to an illustrative embodiment.

DETAILED DESCRIPTION

Figure 2A:
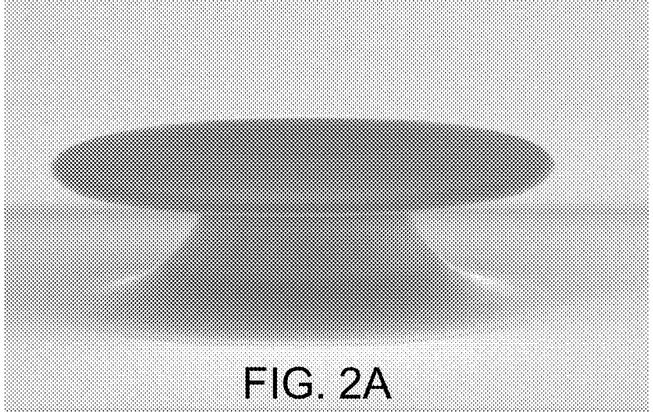
FIG. 2A is an all-glass toroid reflowed using the $CO_2$ laser method.
Figure 2B:
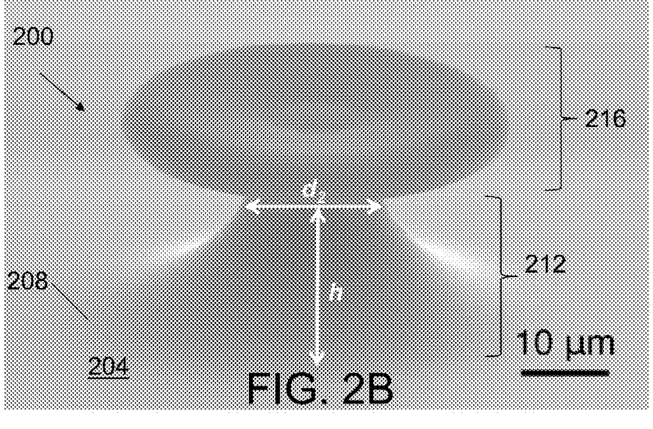
FIG. 2B is an all-glass toroid reflowed using high temperature furnace anneal according to an illustrative embodiment.

Provided herein are optical microresonator platforms and methods for fabricating the platforms. The optical microresonator platforms comprise a substrate having a surface and a $SiO_2$ pillar extending from the surface of the substrate and terminating in a $SiO_2$ optical microresonator. As further described below, the substrate may be a $SiO_2$ substrate. An illustrative optical microresonator platform 200 is shown in FIG. 2B. The optical microresonator platform 200 includes a $SiO_2$ substrate 204 having a surface 208 and a $SiO_2$ pillar 212 extending from the surface 208 and terminating in a $SiO_2$ optical microtoroid 216.

The substrate, the $SiO_2$ pillar and the $SiO_2$ optical microresonator of the optical microresonator platform form a monolithic structure. By "monolithic" it is meant that the substrate, the $SiO_2$ pillar and the $SiO_2$ optical microresonator form a single, continuous structure. Such monolithic structures may originate from a single, common parent body, e.g., a Si coated quartz wafer. This is in contrast to a platform in which one or more individual components are formed separately and subsequently joined together (e.g., via an adhesive material). The optical microresonator platforms may be structurally distinguished from those comprising non-monolithic structures. By way of illustration, cross-sectional images (e.g., scanning electron microscope images) of the optical microresonator platforms may be distinguished from those comprising non-monolithic structures, e.g., by the smoothness of the interfaces formed between individual components (e.g., between the $SiO_2$ pillar and the $SiO_2$ optical microresonator), and/or the lack of a distinct, identifiable interface between individual components (e.g., between the substrate and the $SiO_2$ pillar), and/or the absence of a separate material between adjacent individual components (e.g., an adhesive material). However, the optical microresonator platforms may comprise or may be operably coupled to additional components besides the substrate, the $SiO_2$ pillar and the $SiO_2$ optical microresonator, such additional components which may or may not be formed from a single, common parent body.

The pillar, the optical microresonator, and in some embodiments, the substrate, of the optical microresonator platforms are composed of silica ($SiO_2$). The terms "silica," "$SiO_2$," "oxide," and "glass" are used herein interchangeably. Silica is a robust, chemically inert material, as compared to silicon (Si), which is less biocompatible. In addition, although silicon is highly transparent in the infrared, it absorbs strongly in the visible region (from about 400 nm to about 700 nm), limiting its utility in this region of the electromagnetic spectrum. The use of silica in place of silicon renders the present optical microresonator platforms more desirable for applications including label-free sensing when compared to conventional optical microresonator platforms based on silicon due to its optical transparency in the visible region. In some embodiments, the substrate, the $SiO_2$ pillar and the $SiO_2$ optical microresonator are substantially free of silicon (except for silicon in the form of $SiO_2$). In some embodiments, the substrate, the $SiO_2$ pillar and the $SiO_2$ optical microresonator and are not in thermal contact with silicon (except for silicon in the form of $SiO_2$). Similarly, in some embodiments, the entire optical microresonator platform is substantially free of silicon and/or is not in thermal contact with silicon (except for the silicon in the form of $SiO_2$). The term "substantially" is used in recognition of the fact that the substrate, the $SiO_2$ pillar and the $SiO_2$ optical microresonator may not be perfectly free of Si. For example, these components may comprise some small amount of Si, e.g., due to the fabrication process or due to the nature of the starting materials, but the amount is so small that the properties and functioning of the optical microresonator platform are essentially the same as if the components were perfectly free of Si.

The silica of the components of the optical microresonator platforms may be undoped or doped. By way of illustration, in some embodiments, the $SiO_2$ optical microresonator is doped with a dopant selected to adjust the optical properties (e.g., the resonance frequencies or to generate a lasing medium, thus creating a microlaser) of the $SiO_2$ optical microresonator, depending upon the particular application. Suitable dopants may include Er, Yb, etc.

Figure 4:
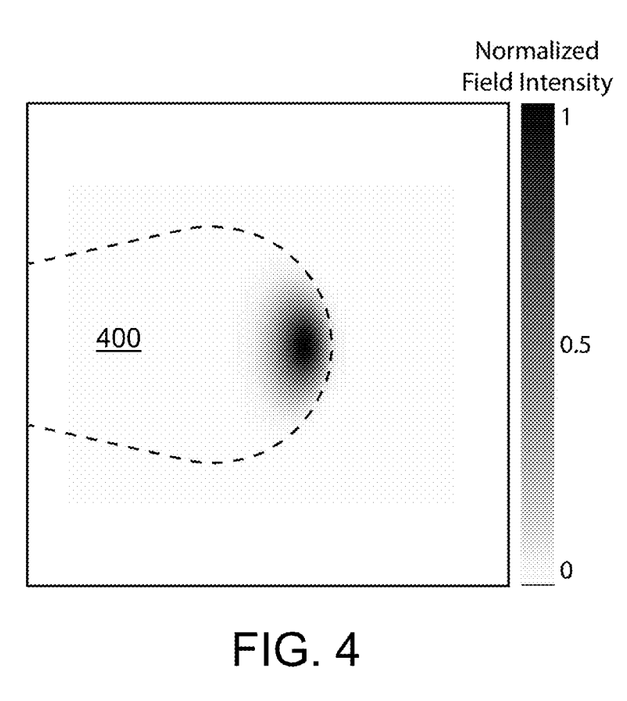
FIG. 4 illustrates a cross-sectional view of the simulated intensity of the principle mode propagating in the rim of an all-glass toroid according to an illustrative embodiment.
Figure 5:
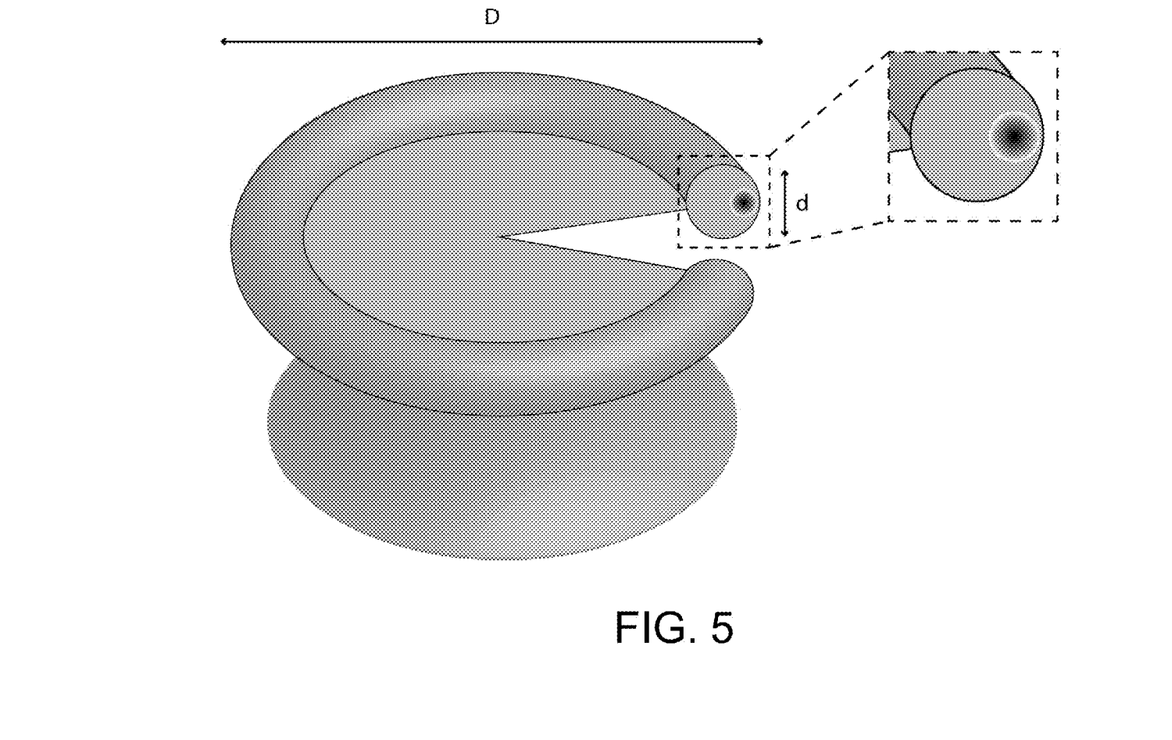
FIG. 5 illustrates a schematic of a conventional $SiO_2$-on-Si toroid.

The $SiO_2$ optical microresonator of the optical microresonator platform is a whispering gallery mode (WGM) optical microresonator which supports modes that circulate the diameter of the optical microresonator in an integral number of wavelengths, known as resonant frequencies. An optical microresonator may be characterized by its resonance frequencies, and by its quality (Q) factor at these frequencies, which equals $\lambda/\Delta\lambda$, where $\lambda$ is resonant wavelength and $\Delta\lambda$ is the linewidth of the resonance at the resonant wavelength. In some embodiments, the $SiO_2$ optical microresonator is characterized by a Q factor of at least about $10^5$. This includes embodiments in which the $SiO_2$ optical microresonator is characterized by a Q factor of at least about $10^6$, at least about $10^7$, at least about $10^8$, at least about $10^9$, in the range of about $10^5$ to about $10^9$. The $SiO_2$ optical microresonators may assume a variety of shapes and sizes, depending upon the particular application and desired Q value. Suitable exemplary shapes include a sphere, a toroid, a disk, a bottle and a capillary. In some embodiments, the SiO$_2$ optical microresonator is a microtoroid having a rim, the rim characterized by a tear-shaped cross-section. As illustrated in FIG. 4, the SiO$_2$ optical microtoroid 216 of FIG. 2B has a rim 400 characterized by a tear-shaped cross-section. This is in contrast to a conventional SiO$_2$-on-Si toroid shown in FIG. 10 which has a rim 1000 characterized by a circular cross-section. As shown in FIG. 5, in general, microtoroids may be characterized by a major diameter D and a minor diameter d. SiO$_2$ optical microtoroids having various major diameters and minor diameters may be used. In some embodiments, the SiO$_2$ optical microtoroid is characterized by a major diameter D in the range of from about 20 μm to about 100 μm.

The SiO$_2$ optical microresonator is supported by a SiO$_2$ pillar extending from the surface of the substrate. The pillars may assume a variety of shapes and sizes. The SiO$_2$ pillars may be characterized by a height h defined by the dimension between the surface of the underlying substrate from which the SiO$_2$ pillar extends and the surface of the overlying SiO$_2$ optical microresonator which extends from the opposing end of the SiO$_2$ pillar. (See FIG. 2B.) The SiO$_2$ pillars may be characterized by a diameter d$_2$ defined by the dimension across the SiO$_2$ pillar at or near the point of connection to the overlying SiO$_2$ optical microresonator. (See FIG. 2B.) As described in the Example below, the diameter d$_2$ may be selected to adjust (e.g., minimize) the mechanical stresses that arise during the oxidation step of the fabrication process, thereby reducing the rippling of the surface of the SiO$_2$ optical microtoroid. In some embodiments, the diameter d$_2$ of the SiO$_2$ pillar is in the range of from about 1 μm to about 30 μm. This includes embodiments in which the diameter d$_2$ of the SiO$_2$ pillar is in the range of from about 10 μm to about 30 μm or from about 10 μm to about 20 μm. As shown in FIG. 2B, the SiO$_2$ pillar may assume a pyramid-like shape. However, SiO$_2$ pillars having more uniform dimensions along their heights may also be used.

Figure 1:
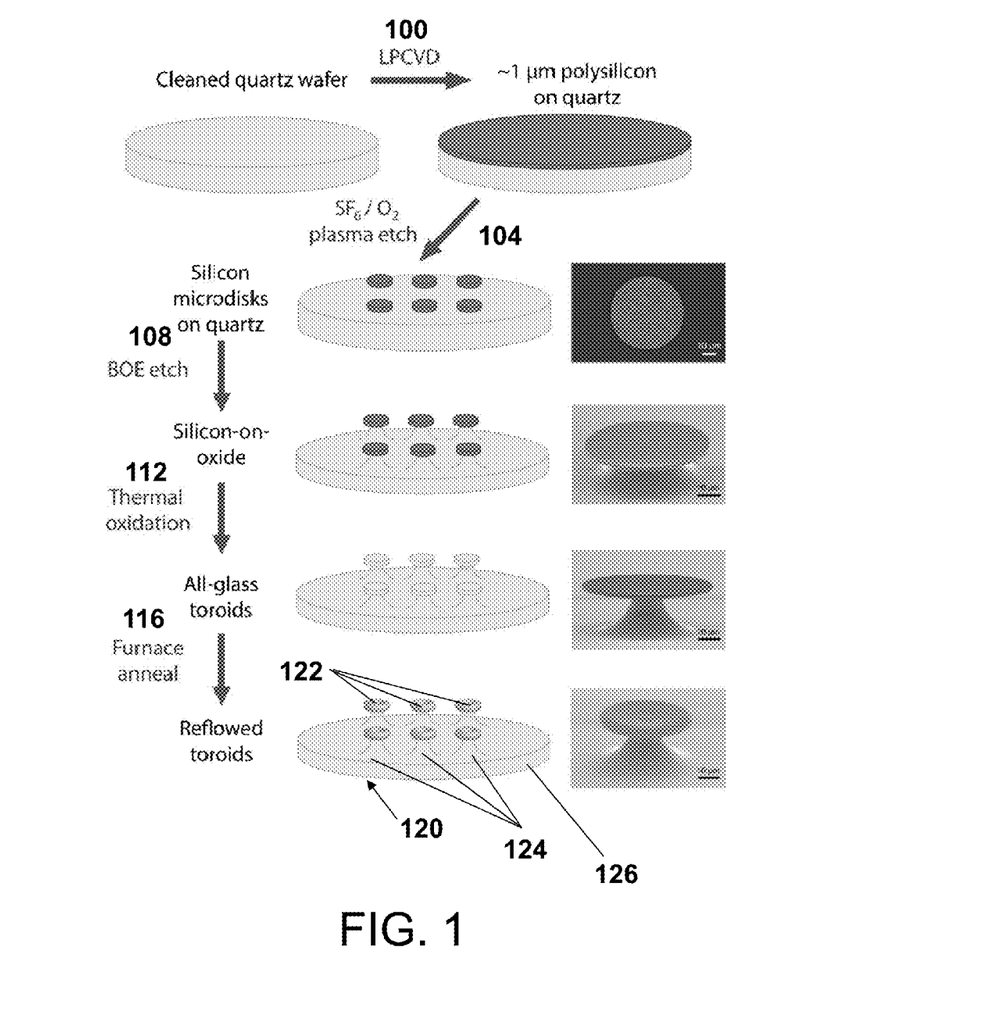
FIG. 1 illustrates a process for fabricating an optical microresonator platform comprising $SiO_2$ microtoroids according to an illustrative embodiment, along with optical micrographs or scanning electron microscope (SEM) images taken along certain steps of the process. Si microdisks are lithographically defined on a $SiO_2$ substrate, thermally oxidized to form an all-glass structure and then thermally reflowed using a high temperature furnace anneal. SEM scale bars are 10 μm.

The optical microresonator platform may comprise a plurality of SiO$_2$ pillars, each SiO$_2$ pillar extending from the surface of the substrate and terminating in a SiO$_2$ optical microresonator. The plurality of SiO$_2$ pillars and their associated SiO$_2$ optical microresonators may be arranged in an array (e.g., a linear array, a rectangular array, etc.). An illustrative optical microresonator platform 120 comprising an array of SiO$_2$ optical microresonators 122 atop SiO$_2$ pillars 124 extending from a SiO$_2$ substrate 126 is shown in FIG. 1.

As described above, the substrate may be a SiO$_2$ substrate. Various SiO$_2$ substrates may be used, e.g., a quartz wafer or coverslip. In some embodiments, however, substrates other than SiO$_2$ substrates may be used, provided the substrate is substantially transparent to visible light (light having a wavelength from about 400 nm to about 700 nm). A substrate may be considered to be substantially transparent to visible light if it exhibits a transparency to visible light which is similar to, or better than, a similarly configured SiO$_2$ substrate. Suitable such substrates include, e.g., sapphire (Al$_2$O$_3$), alumina (Al$_2$O$_3$), titanium dioxide (TiO$_2$), or silicon nitride (Si$_3$N$_4$). Such substrates necessarily do not include silicon substrates, since silicon is not substantially transparent to visible light.

The optical microresonator platform may further comprise additional components. In one embodiment, the optical microresonator platform comprises a waveguide configured to evanescently couple light from a light source into the SiO$_2$ optical microresonator. In some embodiments, the waveguide also forms a monolithic structure with the substrate, the SiO$_2$ pillar and the SiO$_2$ optical microresonator of the optical microresonator platform. The waveguide may be formed from the same, single, common parent body as these other components. The waveguide may comprise a SiO$_2$ support structure extending from the surface of the substrate and terminating in a SiO$_2$ waveguide surface (i.e., the surface that guides electromagnetic waves). The SiO$_2$ support structure may be in the form of an elongated ridge extending along the surface of the substrate. The waveguide may be positioned such that it can evanescently couple light into a plurality of SiO$_2$ optical microresonators simultaneously, e.g., a subset of SiO$_2$ optical microresonators in an array of SiO$_2$ optical microresonators. The optical microresonator platform may comprise a plurality of waveguides, each waveguide configured to evanescently couple light from a light source into an individual SiO$_2$ optical microresonator or into a plurality of SiO$_2$ optical microresonators. Waveguide designs such as those described in Zhang, X. et al., Optics Express, Vol. 21, No. 20, Oct. 7, 2013 may be used.

Methods for fabricating the optical microresonator platforms are also provided. By contrast to conventional methods for forming optical microresonator platforms, at least certain embodiments of the present methods are fully scalable and allow for the high-throughput formation of large arrays of highly uniform SiO$_2$ optical microresonators. In one embodiment, a method comprises patterning a layer of silicon (Si) which has been formed on a surface of a SiO$_2$ substrate to form a silicon island on the surface of the SiO$_2$ substrate; removing a portion of the SiO$_2$ substrate under the silicon island to form a SiO$_2$ pillar supporting the silicon island; and thermally oxidizing the silicon island to form the SiO$_2$ optical microresonator.

As described in the Example, the patterning step may involve standard photolithography techniques, e.g., depositing a layer of photoresist on the silicon layer; exposing the layer of photoresist to UV light; developing the layer of photoresist; etching (e.g., via an anisotropic SF$_6$/O$_2$ plasma etch) the silicon layer; and removing the remaining photoresist material. The shape and size of the silicon island depends upon the desired form of the SiO$_2$ optical microresonator. In order to form a SiO$_2$ optical microtoroid, the silicon island may be a silicon microdisk. The conditions of the SF$_6$/O$_2$ plasma etch may be selected to maximize the smoothness of the sidewalls of the silicon islands (i.e., decreasing the O$_2$ concentration to lower the etch rate). The portion of the SiO$_2$ substrate under the silicon island may be removed by etching (e.g., via an isotropic buffered oxide etch (BOE)). The conditions of the BOE etch step may be selected to provide a desired diameter for the SiO$_2$ pillar. The thermal oxidation step may be carried out by exposing the silicon islands to steam at an elevated temperature (e.g., 1050° C.) sufficient to thermally oxidize the silicon to SiO$_2$.

The method may further comprise exposing the SiO$_2$ optical microresonator to a reflow process in order to smooth the surface of the SiO$_2$ optical microresonator and increase its Q factor. In some embodiments, the reflow process is a thermal reflow process comprising heating (e.g., using a furnace, oven, etc.) the SiO$_2$ optical microresonator to an annealing temperature at a ramping rate and maintaining the annealing temperature for an annealing time. This kind of thermal reflow process using ambient heating is distinguished from a laser reflow process which involves illuminating an optical microresonator with a laser beam. The laser reflow processes cannot be scaled up since it must be conducted on individual optical microresonators, one at a time.

The particular ramping rate, annealing temperature and annealing time may be selected to provide a desired morphology for the $SiO_2$ optical microresonator. A suitable set of conditions for providing a $SiO_2$ optical microtoroid is a ramping rate of from about 2 to about 10° C./min (e.g., about 5° C./min to about 10° C./min, about 8° C./min to about 10° C./min), an annealing temperature of about 1275° C. to about 1350° C. (e.g., about 1300° C. to about 1350° C., 1325° C. to about 1350° C.), and an annealing time of about 2 to about 8 hours (e.g., about 4 to about 8 hours, about 6 to about 8 hours). These conditions represent a narrow window of annealing temperatures and annealing times that result in a toroidal-shaped microresonator. Conditions outside of these ranges will either result in an unreflowed $SiO_2$ disk, which is insufficient for providing the necessary smoothness to elevate the quality factor, or a microresonator structure that begins to approach the form of a spherical or goblet microresonator. Such forms, though possessing high Q factors, result in structures that are very short (due to excessive melting of the pillar) and are difficult to evanescently couple into due to the taper coupling geometry. Additionally, the deviation from the toroidal structure suggests a change in the coupled mode properties (e.g., an extended mode volume), which could negatively influence the sensing capabilities of the device. However, as noted above, other windows of ramping rate, annealing temperature and annealing time may be selected to provide different morphologies for the $SiO_2$ optical microresonator.

If the $SiO_2$ substrate did not already include the layer of silicon on its surface, the method may first comprise forming the silicon layer on the surface of the $SiO_2$ substrate. The layer of silicon may be a layer of polysilicon, which may be deposited using a variety of thin-film deposition techniques, e.g., low-pressure chemical vapor deposition (LPCVD). The layer of silicon may be a layer of single-crystalline silicon. The thickness of the layer of silicon may be selected depending upon the desired morphology and dimensions for the $SiO_2$ optical microresonator.

The method may further comprise forming other components of the optical microresonator platform. By way of illustration, the method may further comprise forming the waveguide described above as a monolithic structure with the $SiO_2$ substrate, the $SiO_2$ pillar and the $SiO_2$ substrate. The patterning and substrate removal steps may be adjusted to provide the components of the waveguide as generally outlined in Zhang, X. et al., Optics Express, Vol. 21, No. 20, Oct. 7, 2013. However, in the present methods, the layer to be patterned is the layer of silicon and the substrate to be removed is $SiO_2$. Thermal oxidation of silicon to $SiO_2$ follows as described above. Finally, the thermal reflow process using ambient heating may be used as described above.

The optical microresonator platforms may also be fabricated via other methods. The completely transparent optical microresonator could also be fabricated using the scheme similar to the fabrication of the $SiO_2$-on-Si resonator, except starting with any of the visibly transparent substrates described above and the deposition of a sol-gel oxide layer to form the resonator. Additionally, a structure identical to a $SiO_2$-on-Si resonator could be used, with additional steps of thermally oxidizing the outer layer of the pillar and substrate, bulk etching the residual silicon, and transferring the leftover oxide layer (containing the optical microresonator and the pillar and, possibly, some of the substrate) to a transparent substrate, such as a glass coverslip. Because of the surface chemistry, the leftover oxide layer and the glass coverslip would be expected to undergo direct bonding, resulting in a single, continuous, monolithic structure.

The optical microresonator platforms find use in label-free sensing applications, single-particle and single-molecule microscopy and spectroscopy, and a variety of other microfluidic and photonics applications. A basic method for using the optical microresonator platform comprises evanescently coupling a probe light beam into the $SiO_2$ optical microresonator, wherein the wavelength of the probe light beam substantially matches at least one resonance frequency of the $SiO_2$ optical microresonator and detecting light from the probe light beam. The light may be detected under a variety of conditions (e.g., exposing the surface of the $SiO_2$ optical microresonator to a sample) to assess whether the conditions result in a shift of the at least one resonance frequency. In another illustration, the optical microresonator platforms may be incorporated into any of the apparatuses for single particle or single molecule spectroscopy described in U.S. application Ser. No. 14/621,502, which is hereby incorporated by reference in its entirety. Such apparatuses may be used for carrying out any of the methods described in U.S. application Ser. No. 14/621,502.

EXAMPLE

This Example demonstrates fabrication of all-glass microtoroid resonators. The morphology leading to the high Q/V of the $SiO_2$-on-Si microtoroid has been preserved and the fabrication, biocompatibility, and optical challenges have been addressed by eliminating the silicon pillar and substrate. Notably, all-glass toroids were reflowed using a high-temperature furnace anneal step, which provides a uniform, efficient and cost-effective wafer-scale reflow mechanism, while preserving the surface tension-induced smoothness of the $SiO_2$-on-Si toroid. Such a high-temperature furnace anneal step is impossible to use with $SiO_2$-on-Si microtoroids due to silicon's substantially lower melting point than silica.

The all-glass toroidal microresonator fabrication is illustrated in FIG. 1, which shows the steps 100-116 in the process along with optical micrographs (step 100) or scanning electron microscope (SEM) images (remaining steps) associated with each of steps 104-116. The first step 100 in the process is the deposition of ~1 μm of polysilicon onto a quartz wafer via low-pressure chemical vapor deposition (LPCVD). In a second step 104, the silicon layer is patterned into an array of 60 μm-diameter disks using photolithography (i.e., a layer of photoresist is deposited onto the polysilicon, followed by exposure to UV light, followed by development of the photoresist). The pattern is transferred to the silicon layer using an anisotropic $SF_6/O_2$ plasma etch, thereby creating silicon microdisks. The conditions of the $SF_6/O_2$ plasma etch may be selected to maximize the smoothness of the sidewalls of the silicon microdisks (i.e., decreasing the $O_2$ concentration to lower the etch rate). Following silicon microdisk formation, in a third step 108, the oxide pillar is etched using an isotropic buffered oxide etch (BOE). The conditions of the BOE etch step may be selected to provide a desired diameter for the $SiO_2$ pillar. Smaller diameters (e.g., about 15 μm versus about 30 pin) were found to relieve the mechanical stresses that arise during high-temperature oxidation, thereby reducing the rippling of the surface of the toroids. In a fourth step 112, once the pillars are etched, the silicon disks can be fully oxidized to $SiO_2$ at 1050° C. in steam (wet oxidation). Optical microscopy was used to confirm full conversion of silicon to $SiO_2$. If desired, the wafer may be diced into pieces that can be integrated into an instrument of choice.

Though thermal oxidation results in some edge smoothing, it does not yield the surface-tension-induced nanometer smoothness required for ultrahigh Q factors. Even after optimizing the conditions of the silicon microdisk etch, residual sidewall roughness remains after oxidation. Because the temperature of the oxidation is not high enough to induce reflow in the rim of the toroid, the pre-reflowed toroids exhibited low Q factors, with average Q factors reaching only the low-$10^4$ regime.

In order to achieve high Q factors, all-glass toroidal resonators were reflowed to smooth the surface of the rim of the toroid, and eliminate any outstanding roughness from the etch step. As shown in FIG. 2A, initial attempts to reflow the microresonator with a similar $CO_2$ laser-induced reflow used in $SiO_2$-on-Si toroid fabrication resulted in a variety of mushroom-like shapes, with high irreproducibility between individual toroids. In $SiO_2$-on-Si toroids, the silicon pillar effectively cools the center of the toroid when the resonator is illuminated with the $CO_2$ laser. This cooling, along with the thermal isolation of the rim, results in a selective melting around the rim. In all-glass toroids, the lack of the silicon pillar as a heat sink results in an even melting of the entire structure. Though the degree of melting can be controlled by adjusting the laser power, the process is highly sensitive and extremely variable between toroids, even between those on the same chip. The highest attainable Q factors of laser-reflowed microtoroids were in the low-$10^5$ regime.

Figure 3:
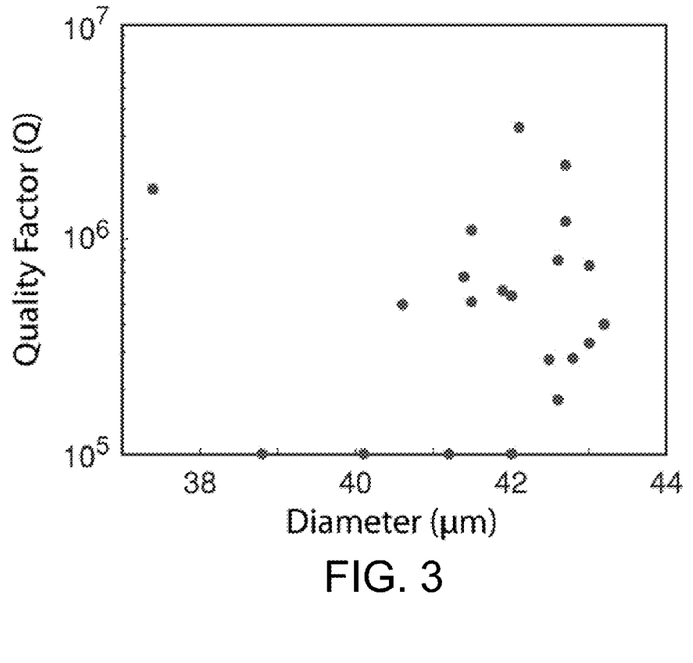
FIG. 3 is a graph showing the measured quality factors of several all-glass toroids according to an illustrative embodiment.

To provide a more controlled and reproducible reflow environment, a high temperature furnace anneal (step 116 in FIG. 1) was designed and conducted on the chip-scale. The furnace anneal was conducted in air in a high temperature box furnace. The optimal conditions were determined to be a 7.5 hour hold at 1350° C., with a ramp rate of 10° C./min. However, the continuum between microsphere and toroidal morphologies were achieved by adjusting the temperature and hold time. The resulting structures were characterized using optical microscopy and scanning electron microscopy (SEM). An illustrative all-glass toroid is shown in FIG. 2B. The high temperature furnace anneal resulted in a uniform, toroidal structure of all of the toroids on the chip, and was replicated on multiple chips of toroids. The controlled environment in the furnace allows for the temperature to be precisely set at the reflow point of thermal oxide. Additionally, the amount of time at this critical temperature can be adjusted to control the degree of reflow. As shown in FIG. 3, the high temperature furnace reflow provided all-glass toroids having Q factors in excess of $1\times10^6$.

Figure 6:
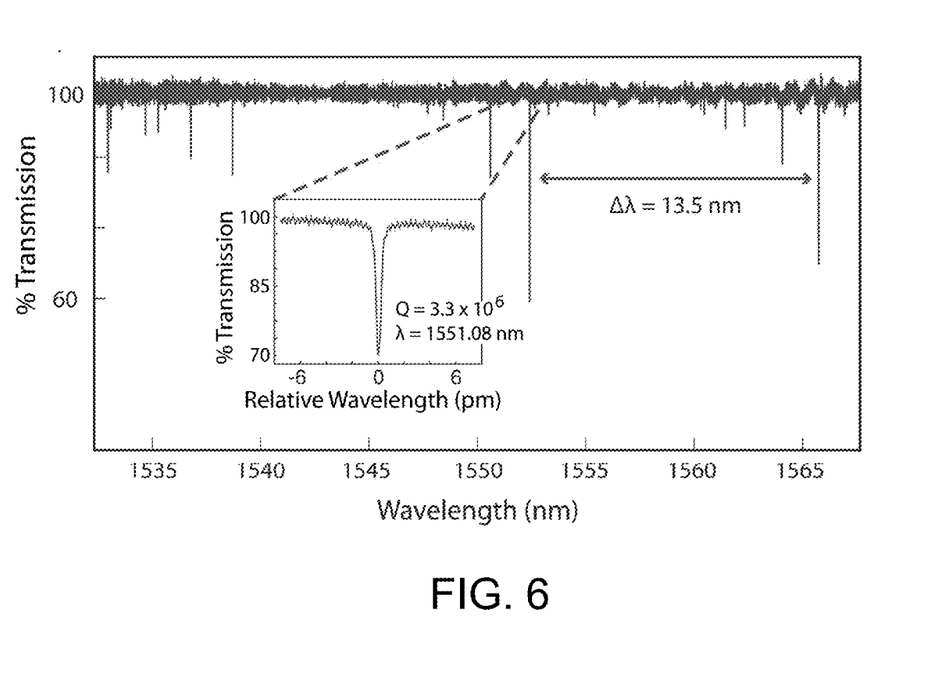
FIG. 6 shows a mode spectrum measurement of an all-glass toroid according to an illustrative embodiment.
Figure 10:
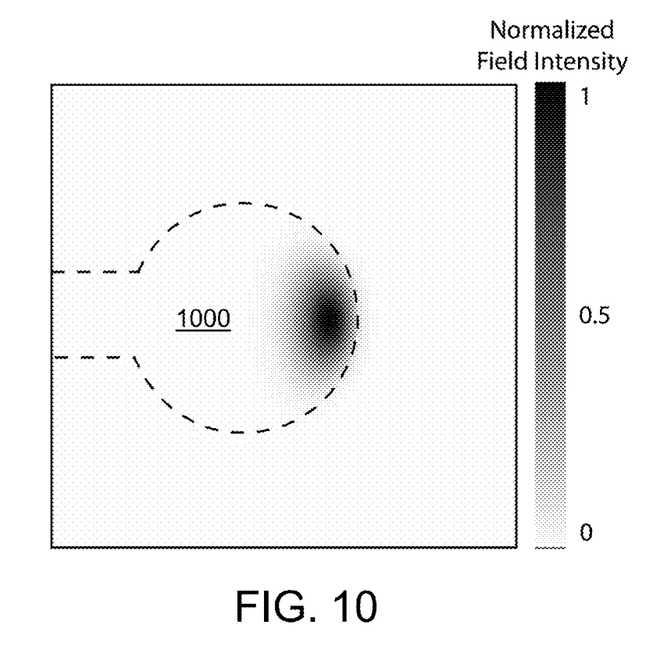
FIG. 10 illustrates a cross-sectional view of the simulated intensity of the principle mode propagating in the rim of a conventional $SiO_2$-on-Si toroid.

Though the structure of the furnace reflowed all-glass resonators is more toroidal in nature when compared to its laser reflowed all-glass analog, the furnace reflowed all-glass resonators exhibit minor structural differences when compared with conventional $SiO_2$-on-Si toroids. The main difference is the lack of high curvature defining the minor diameter in the all-glass toroid. As shown in FIG. 4, to assess whether this morphological difference significantly affects the structure of the coupled mode, finite element simulations using the COMSOL multiphysics package were used to simulate the mode structure at the rim of the all-glass toroid. FIG. 4 also shows a schematic cross-section of the rim of an all-glass toroid formed using the process of FIG. 1 (the cross-section taken perpendicular to the plane of the all-glass toroid). For comparison, FIG. 5 provides a schematic illustration of a conventional $SiO_2$-on-Si toroid. FIG. 5 also labels the major diameter D and the minor diameter d and shows the mode volume (the space occupied by the propagating mode) at the rim of the toroid. These figures show that rim of the all-glass toroid (FIG. 4) has a tear drop cross-sectional shape, while the rim of the conventional $SiO_2$-on-Si toroid has a circular shape (FIGS. 5 and 10). However, despite this structural difference, the simulation results gave a mode volume of 300 $\mu m^3$ for the all-glass toroid, which is slightly smaller than the mode volume of and $SiO_2$-on-Si toroid of comparable minor diameter (315 $\mu m^3$). As shown in FIG. 4, the simulations also revealed that the mode is still constrained to the outer edge of the rim, and looks highly similar to that of a $SiO_2$-on-Si toroid (FIGS. 5 and 10). As shown in FIG. 6, the mode spectrum of the reflowed all-glass toroids was characterized and the free spectral range (FSR) of the toroid was experimentally determined to be 13.5 nm, which is in good agreement with the calculated FSR, 12.9 nm. Critically the mode spectrum is uncongested, indicating that the reduction of modes due to the more planar nature of the all-glass toroid is still occurring despite the morphological differences. The small mode volume and uncongested mode spectra demonstrate that the advantages of the toroid structure can be present in an all-glass microstructure, with the additional advantage of chip-scale fabrication.

The highest Q factors achieved for the all-glass toroids, in the mid-$10^6$ range, are comparable to the values seen in the majority of single-molecule and single-particle detection and microscopy studies. However, the materials-limited Q factor is substantially higher, and $SiO_2$-on-Si have been produced with Q factors exceeding $10^8$. Three main sources limit the Q factor: bending losses, scattering losses and materials losses. Bending losses become relevant and Q factors decrease significantly as the major diameter decreases below a threshold determined by wavelength. Scattering losses increase as the roughness in the rim increases, with scattering losses negligible after reflow. The major diameters here are large enough to make bending losses negligible while SEM images indicate the furnace reflow eliminates surface roughness, suggesting the Q factor is materials loss limited (FIG. 2B).

One potential contributor to materials absorption in all-glass toroids is devitrification, the crystallization of vitreous oxide into cristobalite as the silica is heated and cooled. Nucleation of these crystals is often initiated as a result of contamination on the glass surface, and occurs at temperatures of 800° C. and above. Optical loss due to cristobalite formation has been shown to increase linearly with annealing time, and can result in substantial optical losses, largely from the effect of cristobalite scattering centers. Rapid heating and cooling, establishing a contaminant free environment, and minimizing the time spent at high temperatures all serve to minimize devitrification, but may not eliminate it completely. There is also evidence that the material properties of oxide grown from single-crystalline silicon are different from that of oxide grown from polysilicon, which may be limiting the Q factor.

Figure 7:
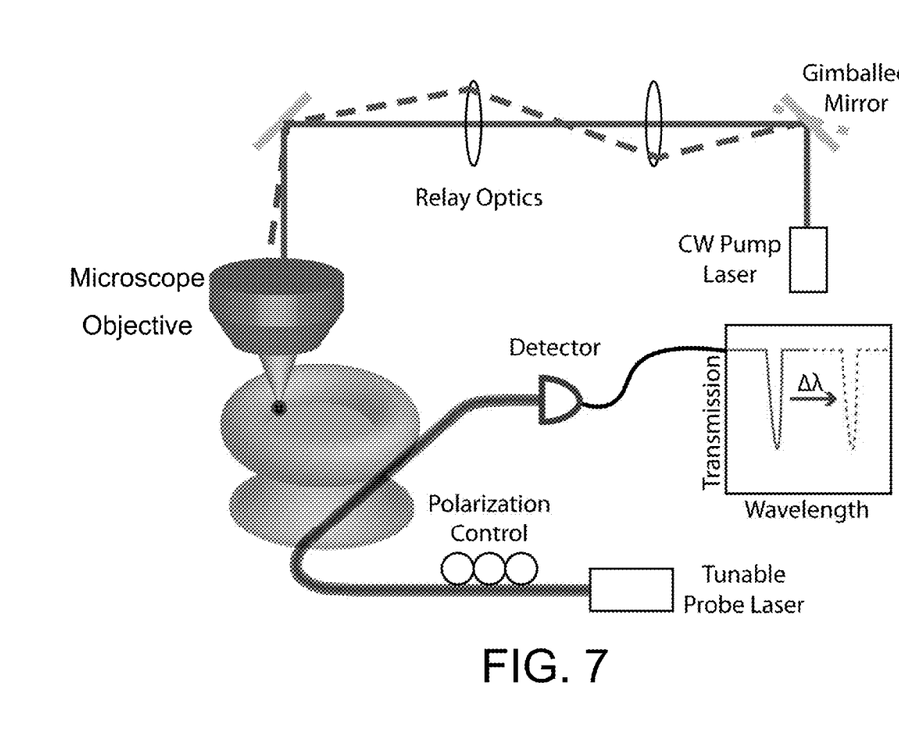
FIG. 7 is an illustration of the instrumental design for conducting photothermal microscopy using all-glass toroids according to an illustrative embodiment.

The all-glass toroids were used for photothermal imaging. The experimental set-up is schematically illustrated in FIG. 7 and employs a two-beam design. Light from the probe beam (fiber coupled, tunable laser, 1550 nm band) is evanescently coupled into the rim of the resonator using a tapered optical fiber supporting a single air-guided mode. The pump beam (free space, 635 nm, 1 mW incident power) excites nano-objects on the surface of the resonator. As the objects relax, they dissipate heat into their local microenvironment, inducing a shift in the resonant wavelength of the all-glass microtoroid. This resonance shift is detected and can be used to image the objects present.

Figure 8A:
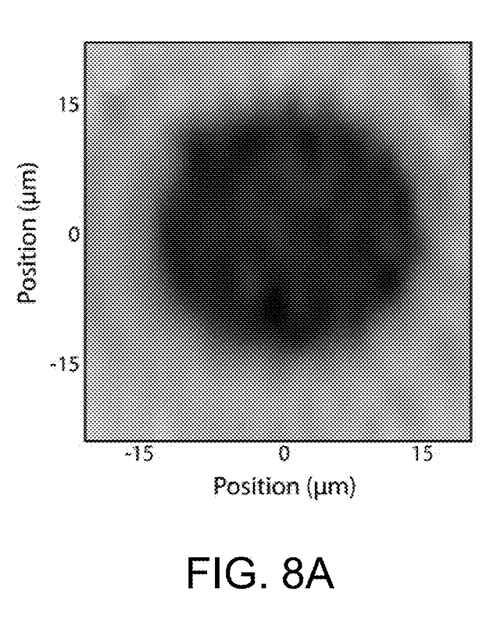
FIGS. 8A-8B provide a background photothermal comparison of a $SiO_2$-on-Si toroid (FIG. 8A) and an all-glass toroid according to an illustrative embodiment (FIG. 8B). The inset in FIG. 8B is the background of the all-glass toroid on a meaningful scale.
Figure 8B:
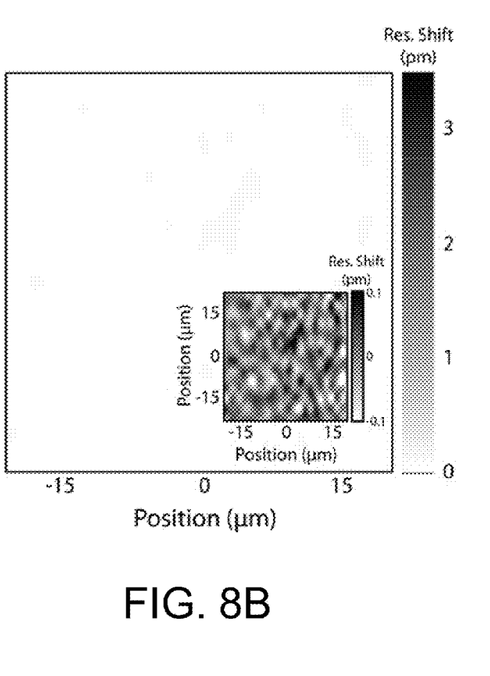

In order to demonstrate the advantages of using all-glass microtoroids for label-free single-particle photothermal microscopy, large area maps of clean $SiO_2$-on-Si and all-glass toroids were taken to compare the background photothermal absorption of the two devices (FIGS. 8A-8B). The background photothermal absorption of the all-glass toroid is low and highly uniform at 635 nm and indicates complete oxidation of the polysilicon during fabrication, resulting in a device that is transparent in the visible region (FIG. 8B). When compared to the background of an oxide-on-silicon toroid (FIG. 8A), the background of the all-glass toroid is essentially non-existent, confirming the major optical advantage of the all-glass toroid for label-free sensing.

Figure 9A:
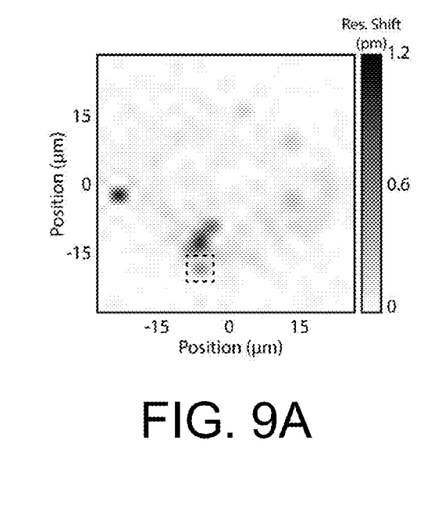
FIG. 9A is a large area map of an all-glass toroid with gold nanorods deposited on the surface.
Figure 9B:
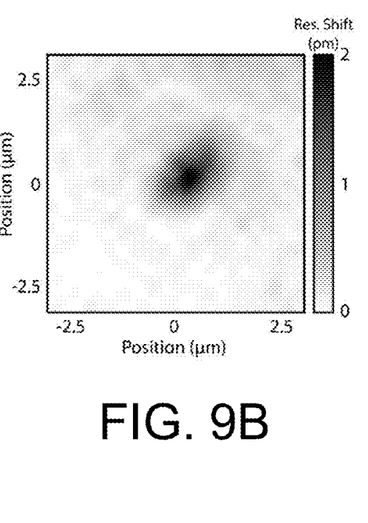
FIG. 9B is a high-resolution map of an individual gold nano rod (the object at 6 o'clock on the large area map).
Figure 9C:
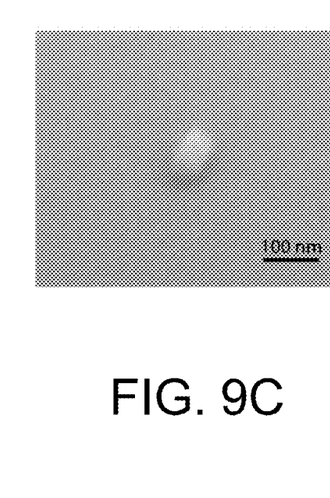
FIG. 9C is an SEM image of the same gold nanorod.

To further demonstrate the utility of the all-glass microtoroids for photothermal microscopy, individual gold nanorods (40 nm×80 nm) were deposited on the microresonator. As shown in FIG. 9A, large area photothermal maps were used to locate nanorods on the surface of the microresonator. As shown in FIG. 9B, once nanorods are located, hi-resolution maps can be taken to image individual nanorods, and can be used to determine morphology, orientation, and absolute absorption cross-section. (See Heylman, K.; Knapper, K.; Goldsmith, R., Photothermal Microscopy of Non-luminescent Single Particles Enabled by Optical Microresonators. *Journal of Physical Chemistry Letters* 2014, 5 (11), 1917-1923). Notably, these images were produced not by measuring emitted or transmitted light, but by using the microresonator to quantify the heat dissipated by the gold nanorod after photoexcitation, a powerful strategy for label-free imaging. The substantial reduction in background facilitates single-molecule label-free imaging and spectroscopy to provide label-free spectroscopic identification, a powerful augmentation to label-free sensing.

All-glass toroidal microresonators represent a remarkable step forward in the challenge of label-free imaging and measurement. A visibly-transparent device enables the investigation of the many important systems that have absorption features in the visible region, including biological systems and photoresponsive materials. By significantly lowering the background absorption in the region, all-glass toroids make single-molecule sensing more feasible. The added imaging capabilities provide a powerful technique for characterizing individual members of complex systems and allow for probing surface heterogeneity at the single-molecule level. In complement to the added measurement advantages, the fabrication challenges overcome in the fabrication process of the all-glass toroid over its counterparts—the elimination of silicon and the introduction of the chip-scale furnace reflow—facilitates widespread integration of these devices as sensors in all sorts of measurement applications, allowing label-free techniques to be used on a much broader scale.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. An optical microresonator platform comprising a substrate having a surface, a plurality of $SiO_2$ pillars, and a plurality of $SiO_2$ whispering gallery mode (WGM) optical microresonators, each $SiO_2$ pillar extending from the surface of the substrate and terminating in a corresponding $SiO_2$ WGM optical microresonator of the plurality of $SiO_2$ WGM optical microresonators, wherein the substrate, the plurality of $SiO_2$ pillars and the plurality of $SiO_2$ WGM optical microresonators form a monolithic structure, and further wherein the substrate is substantially transparent to visible light.

2. The optical microresonator platform of claim 1, wherein the substrate is a $SiO_2$ substrate.

3. The optical microresonator platform of claim 1, wherein the plurality of $SiO_2$ pillars and the plurality of $SiO_2$ WGM optical microresonators are arranged in an array.

4. The optical microresonator platform of claim 1, wherein each $SiO_2$ WGM optical microresonator of the plurality of $SiO_2$ WGM optical microresonators is a $SiO_2$ optical microtoroid or a $SiO_2$ optical microsphere.

5. The optical microresonator platform of claim 1, wherein each $SiO_2$ WGM optical microresonator of the plurality of $SiO_2$ WGM optical microresonators is a $SiO_2$ optical microtoroid.

6. The optical microresonator platform of claim 5, wherein each $SiO_2$ optical microtoroid has a rim characterized by a tear-shaped cross-section.

7. The optical microresonator platform of claim 5, wherein each $SiO_2$ optical microtoroid is characterized by a major diameter D in the range of from about 20 µm to about 60 µm and each $SiO_2$ pillar is characterized by a diameter $d_2$ in the range of from about 10 µm to about 20 µm.

8. The optical microresonator platform of claim 1, further comprising one or more waveguides, each waveguide configured to evanescently couple light from a light source into one or more of the plurality of $SiO_2$ WGM optical microresonators, wherein each waveguide is part of the monolithic structure.

9. The optical microresonator platform of claim 1, wherein the substrate is a $SiO_2$ substrate, further wherein the plurality of $SiO_2$ pillars and the plurality of $SiO_2$ WGM optical microresonators are arranged in an array, and further wherein each $SiO_2$ WGM optical microresonator of the plurality of $SiO_2$ WGM optical microresonators is a $SiO_2$ optical microtoroid.

10. The optical microresonator platform of claim 9, further comprising one or more waveguides, each waveguide configured to evanescently couple light from a light source into one or more of the plurality of $SiO_2$ WGM optical microresonators, wherein each waveguide is part of the monolithic structure.

11. An optical microresonator platform comprising a substrate having a surface, a $SiO_2$ pillar extending from the surface of the substrate and terminating in a $SiO_2$ optical microtoroid, wherein the substrate, the $SiO_2$ pillar and the $SiO_2$ optical microtoroid form a monolithic structure, and further wherein the substrate is substantially transparent to visible light.

12. The optical microresonator platform of claim 11, wherein the substrate is a $SiO_2$ substrate.

13. The optical microresonator platform of claim 11, wherein the $SiO_2$ optical microtoroid has a rim characterized by a tear-shaped cross-section.

14. The optical microresonator platform of claim 11, wherein the $SiO_2$ optical microtoroid is characterized by a major diameter D in the range of from about 20 μm to about 100 μm and the $SiO_2$ pillar is characterized by a diameter $d_2$ in the range of from about 10 μm to about 20 μm.

15. The optical microresonator platform of claim 11, further comprising a waveguide configured to evanescently couple light from a light source into the $SiO_2$ optical microtoroid, wherein the waveguide is part of the monolithic structure.

16. A method of fabricating an optical microresonator platform, the method comprising:
  (a) patterning a layer of silicon which has been formed on a surface of a $SiO_2$ substrate to form a plurality of silicon islands on the surface of the $SiO_2$ substrate;
  (b) removing a portion of the $SiO_2$ substrate under each silicon island of the plurality of silicon islands to form a plurality of $SiO_2$ pillars, each $SiO_2$ pillar supporting a corresponding silicon island of the plurality of silicon islands; and
  (c) thermally oxidizing each silicon island of the plurality of silicon islands to convert the silicon of the silicon island to $SiO_2$ to form a plurality of $SiO_2$ WGM optical microresonators, thereby providing the optical microresonator platform comprising the $SiO_2$ substrate having the surface, the plurality of $SiO_2$ pillars, and the plurality of $SiO_2$ WGM optical microresonators, each $SiO_2$ pillar extending from the surface of the $SiO_2$ substrate and terminating in a corresponding $SiO_2$ WGM optical microresonator of the plurality of $SiO_2$ WGM optical microresonators, wherein the $SiO_2$ substrate, the plurality of $SiO_2$ pillars and the plurality of $SiO_2$ WGM optical microresonators form a monolithic structure.

17. The method of claim 16, further comprising performing a thermal reflow process comprising heating the plurality of $SiO_2$ WGM optical microresonators to an annealing temperature at a ramping rate and maintaining the annealing temperature for an annealing time.

18. The method of claim 17, wherein the annealing temperature is in the range of from about 1275 to about 1350° C., the ramping rate is in the range of from about 2 to about 10° C./min, and the annealing time is in the range of from about 2 to 8 hours.

19. The method of claim 16, further comprising, prior to step (a), forming the layer of silicon on the surface of the $SiO_2$ substrate.

20. The method of claim 19, wherein the layer of silicon is a layer of polysilicon.

* * * * *